United States Patent [19]

DeGoler

[11] 4,280,813

[45] Jul. 28, 1981

[54] ANIMAL TATTOOING PASTE AND METHOD OF MAKING THE SAME

[76] Inventor: Warren H. DeGoler, 42 Ginger Cove Rd., Valley, Nebr. 68064

[21] Appl. No.: 104,813

[22] Filed: Dec. 18, 1979

[51] Int. Cl.³ .......................... D06P 1/613; D06P 1/46
[52] U.S. Cl. ............................................. 8/404; 106/22
[58] Field of Search ............................... 8/404; 106/22

[56] References Cited

U.S. PATENT DOCUMENTS

| | | | |
|---|---|---|---|
| 1,868,071 | 7/1932 | Paddock | 106/22 |
| 2,821,821 | 2/1958 | Yen | 106/22 |
| 3,431,122 | 3/1969 | Wilson | 106/22 |
| 3,475,187 | 10/1969 | Kane | 106/22 |

Primary Examiner—Joseph L. Schofer
Assistant Examiner—Maria Parrish Tungol
Attorney, Agent, or Firm—Zarley, McKee, Thomte, Voorhees & Sease

[57] ABSTRACT

An improved animal carcass tattooing paste having substantially enhanced permanency when used to place identifying marks on carcasses, comprising from about 0.05% by weight to about 10.0% by weight of a sorbitan mono-fatty acid ester, from about 0.05% by weight to about 10.0% by weight of a water soluble polyoxyethylene derivative of a fatty acid partial ester of sorbitol, from about 10.0% to about 49.0% by weight of propylene glycol, from about 10.0% to about 49.0% by weight of white mineral oil, from about 1% to about 10% by weight of a thickening agent, from about 0.1% by weight to about 10.0% by weight of inorganic viscosity modifier, from about 0.05% by weight to about 10.0% by weight of an organic dye material which is compatible with the other ingredients of said paste, and from about 1.0% to about 25.0% by weight water. The method comprises the steps of: (1) mixing the water soluble polyoxyethylene derivative of a fatty acid partial ester of sorbitol with heated water; (2) mixing the organic dye material into the mixture; (3) mixing thickening agent, propylene glycol and heated sorbitan mono fatty acid ester and adding the same to the mixture of step (2); (4) mixing the white mineral oil into the mixture of step (3); (5) cooling the mixture and (6) packaging the cooled product.

5 Claims, No Drawings

ANIMAL TATTOOING PASTE AND METHOD OF MAKING THE SAME

BACKGROUND OF THE INVENTION

This invention relates to an animal tattooing paste and more particularly to tattooing paste which is used on hog carcasses.

In normal meat packing operations, hog carcasses are "tattooed" with an identification number sometime before or immediately after slaughter so that the source of the carcass can be determined should the carcass subsequently be found to be diseased or if the animal is bought on a "weight and yield" basis. If the animal is found to be diseased, the U.S.D.A. must ascertain the source of the animal so that further investigation may be conducted.

It is not a matter of simply tattooing an identification number on the carcass since the carcass undergoes extensive processing and ordinary ink is quickly eradicated. The carcasses are normally subjected to scalding water and brush action or flail action to remove the hair from the skin of the carcass. The scalding water quickly dissolves the ink with the brushes and flails completing the eradication of the number.

A further consideration is that the tattooing ink or paste must not contain any ingredient which is carcinogenic, or which may be suspected of being carcinogenic.

Therefore, it is a principal object of this invention to provide an animal tattooing paste which will not be removed from the carcass during the packing process.

A further object of the invention is to provide an animal tattooing paste which does not contain any carciogenic ingredients.

A further object of the invention is to provide an animal tattooing paste which permits the packaging of the same for subsequent distribution and use.

A further object of the invention is to provide an animal tattooing paste which is a food grade product.

A further object of the invention is to provide a thick product that is easy to work with and does not splatter, which remains thick in summer yet will not freeze in winter.

These and other objects will be apparent to those skilled in the art.

DESCRIPTION OF THE PREFERRED PASTE AND METHOD

The animal paste of this invention is formulated or manufactured as follows and unless otherwise stated, the percentages given herein are all weight percent. Tap water is first heated to approximately 180° F. and added to a stainless steel mixing vessel equipped with a stainless steel mixing rod equipped with two, three-bladed propellers. The propellers should be located at the bottom and midpoint of the vessel. An emulsifier and surface agent comprised of a polyoxyethylene derivative of fatty acid partial esters of sorbitol anhydrides is then added to the water and rapidly mixed or agitated. The preferred emulsifier and surface agent is polysorbate 80 which is marketed by ICI under the tradename or trademark Tween 80. A water soluble, carcass permeable dye, preferably black aluminum lake dye, is then added to the water-polysorbate 80 mixture and the resultant mixture continually agitated. An inorganic viscosity modifier is then heated to approximately 200° F. in a stainless steel vessel and added to the white mineral oil. The preferred inorganic viscosity modifier is polybutene having a molecular weight of 2500 marketed by Exxon Chemical Co. under the trademark Peratac. Propylene glycol and an emulsifier and surface active agent comprised of fatty acid ester of sorbitol (previously heated to approximately 180° F.) are then added to the polybutene-mineral oil mixture and mildly agitated to insure complete mixing. The preferred fatty acid ester of sorbitol is sorbitan monostearate manufactured by ICI under the trademark Span 60.

Carboxymethyl-cellulose is then slowly added to the resultant mixture which should be initially agitated at approximately 200 R.P.M. The rate of agitation is increased steadily to approximately 1725 R.P.M. by the time the carboxymethyl-cellulose addition is complete. The resultant mixture is then agitated for another five minutes. The mixture is then permitted to cool and the product is packaged.

EXAMPLE I 7.0% tap water was first heated to approximately 180° F. and added to a stainless steel mixing vessel such as that previously described. 18.75% polysorbate 80 and 31.0% propylene glycol was then added to the water and rapidly agitated or mixed. 3.5% black aluminum lake dye was then added to the water-polysorbate 80-glycol mixture and the resultant mixture agitated. 0.40% polybutene was then heated to approximately 200° F. in a stainless steel vessel and added to a 37.0% mineral oil and 0.75% sorbitan monstearate (previously heated to approximately 180° F.) mixture and mildly agitated to insure complete mixing.

The polybutene, mineral oil and sorbitan monstearate mixture was then slowly added to the hot water, polysorbate 80 and black aluminum lake dye mixture and rapidly agitated at approximately 1725 R.P.M. for approximately five minutes after the two mixtures had been combined. 1.6% carboxymethyl-cellulose was then added slowly to the resultant mixture and was initially agitated at approximately 200 R.P.M. The rate of agitation was increased steadily to approximately 1725 R.P.M. to coincide with the time the carboxymethyl-cellulose addition was complete. The resultant mixture was then agitated for another five minutes, permitted to cool and then packaged.

The tattoo paste of Example I was then employed with a conventional tattooing device which tattooed the carcass with a suitable identification number. The identification number was placed on the carcass up to three days prior to or immediately after the animal was slaughtered and was very legible even after the carcass had been scalded and brushed to remove the hair therefrom.

Table A hereinafter discloses the permissible ranges of the ingredients of the tattoo paste of this invention while Table B discloses the preferred proportions of the paste. Although the ranges of Table A will produce a satisfactory tattoo paste, the proportions of Table B result in a more superior product. It should also be noted that the agitation speeds and periods described hereinabove are preferred but some deviations therefrom may be possible with a somewhat less desirable product resulting therefrom.

Table C identifies the ingredients employed in the manufacture of the tattoo paste by tradename (or trademark) as well as the manufacturer thereof.

TABLE A

| Preferred Ingredients | Permissible Range-Weight % |
| --- | --- |
| Sorbitan Monostearate | .05% to 10.0% |
| Polysorbate 80 | .10% to 30.0% |
| Carboxymethyl-Cellulose | .10% to 10.0% |
| Polybutene | .10% to 10.0% |
| Black Aluminum Lake Dye | .05% to 10.0% |
| Water | 1.00% to 25.0% |
| White Mineral Oil | 10.00% to 49.0% |
| Propylene Glycol | 10.00% to 49.0% |

TABLE B

| Preferred Ingredients | Permissible Proportions-Weight % |
| --- | --- |
| Sorbitan Monostearate | .75% |
| Polysorbate 80 | 18.75% |
| Carboxymethyl-Cellulose | 1.60% |
| Polybutene | .40% |
| Black Aluminum Lake Dye | 3.50% |
| Water | 7.00% |
| Propylene Glycol | 31.00% |
| White Mineral Oil | 37.00% |
|  | 100.00% |

TABLE C

| Chemical Name | Tradename | Manufacturer |
| --- | --- | --- |
| Sorbitan Monostearate | Span 60 | ICX |
| Polysorbate 80 | Tween 80 | ICI |
| Carboxymethyl-Cellulose | CMC | H. Kohnstamm & Co. |
| Polybutene | Peratac | Exxon Chemical Co. |
| Black Aluminum Lake Dye | Jetine Dye | H. Kohnstamm & Co. |
| White Mineral Oil | 85 T | Sonneborn Co. |
| Propylene Glycol | — | Union Carbide |

I claim:

1. The method of manufacturing an improved animal carcass tattooing paste having substantially enhanced permanency when used to place identifying marks on carcasses, comprising the steps of:

(1) adding a polyoxyethylene derivative of a fatty acid partial ester of sorbitol anhydrides and an organic dye material, which is compatible with the other ingredients of the paste, to heated water and propylene glycol and mixing the same;

(2) adding mineral oil and a sorbitan mono fatty acid ester to a heated inorganic viscosity modifier and mixing the same;

(3) adding the mixture of step (2) to the mixture of step (1) and mixing the same;

(4) adding a thickening agent to the mixture and mixing the same; and (5) packaging the product.

2. An improved animal carcass tattooing paste having substantially enhanced permanency when used to place identifying marks on carcasses, comprising from about 0.05% weight to about 10.0% by weight of a sorbitan mono-fatty acid ester, from about 0.10% by weight to about 30.0% by weight of a water soluble polyoxyethylene derivative of a fatty acid partial ester of sorbitol anhydrides, from about 10.0% to about 49.0% by weight of propylene glycol, from about 10.0% to about 49.0% by weight of white mineral oil, from about 1.0% to about 10.0% by weight of a thickening agent, from about 0.1% by weight to about 10.0% by weight of polybutene having a molecular weight of 2500, from about 0.05% by weight to about 10.0% by weight of an organic dye material which is compatible with the other ingredients of said paste, and from about 1.0% to about 25.0% by weight water.

3. An improved animal carcass tattooing paste having substantially enhanced permanency when used to place identifying marks on carcasses comprising 0.75% sorbitan monostearate, 18.75 polyoxyethylene derivative of fatty acid partial esters of sorbitol anhydrides, 31.0 propylene glycol, 37.0% white mineral oil, 1.6% carboxymethyl-cellulose, 0.4% polybutene having a molecular weight of 2500, 3.5% black aluminum lake dye and 7.0% water.

4. The method of manufacturing an animal tattooing paste comprising the steps of:

(1) adding an emulsifier surface agent comprised of a polyoxyethylene derivative of fatty acid partial esters of sorbitol anhydrides and propylene glycol to water which has been heated to approximately 180° F. and mixing the same;

(2) adding black aluminum lake dye to the mixture of step (1) and mixing the same;

(3) heating polybutene having a molecular weight of 2500 to approximately 200° F.;

(4) heating sorbitan monstearate and white mineral oil to approximately 180° F.;

(5) mixing the heated polybutene, sorbitan monostearate and white mineral oil;

(6) adding the mixture of step (5) to the mixture of step (2) and mixing the same;

(7) adding carboxymethyl-cellulose to the mixture of step (6) and mixing the same; and (8) packaging the product for subsequent use.

5. The method of claim 4 wherein the ingredients are added to the mixture in the following amounts:

(a) 0.05 to 10.0% sorbitan monostearate;
(b) 0.10 to 30.0% emulsifier and surface agent;
(c) 10.0% to 49.0% white mineral oil;
(d) 10.0% to 49.0% propylene glycol;
(e) 0.01 to 10.0% carboxymethyl-cellulose;
(f) 0.10 to 10.0% polybutene;
(g) 0.05 to 10.0% black aluminum lake dye; and
(h) 1.0% to 25.0% water.

* * * * *